United States Patent [19]

Fink et al.

[11] Patent Number: 5,063,154

[45] Date of Patent: Nov. 5, 1991

[54] PHEROMONE - INDUCIBLE YEAST PROMOTER

[75] Inventors: Gerald R. Fink, Brookline, Mass.; Joshua Trueheart, San Francisco, Calif.; Elaine A. Elion, Somerville, Mass.

[73] Assignee: Whitehead Institute for Biomedical Research, Cambridge, Mass.

[21] Appl. No.: 212,270

[22] Filed: Jun. 24, 1988

Related U.S. Application Data

[63] Continuation-in-part of Ser. No. 66,078, Jun. 24, 1987, abandoned.

[51] Int. Cl.$^5$ ............... C12N 1/19; C12N 15/31; C12N 15/81
[52] U.S. Cl. ............... 435/69.1; 435/69.9; 435/71.1; 435/91; 435/121; 435/172.1; 435/172.3; 435/256; 435/320.1; 435/940; 536/27; 935/6; 935/8; 935/9; 935/10; 935/22; 935/33; 935/34; 935/37; 935/47; 935/52; 935/59; 935/69
[58] Field of Search ............... 536/27; 435/68, 71.1, 435/91, 171, 172.1, 172.3, 256, 320, 940; 935/1, 6, 8, 9, 10, 22, 33, 34, 36, 37, 47, 48, 52, 55, 56, 59, 60, 61, 66, 68, 69, 69.1, 69.9

[56] References Cited

U.S. PATENT DOCUMENTS 4,615,974 6/1986 Kingsman et al. ............... 435/68

FOREIGN PATENT DOCUMENTS

EP0123544 11/1984 European Pat. Off. .
EPA20183350 8/1986 European Pat. Off. .

OTHER PUBLICATIONS

Hagen et al., 1984, *J Mol Biol*, 178:835-852.
Bresch et al., 1968, *Mol Gen Genet*, 102(4): 301-306.
Bender, A. and Sprague, G. F., Jr., *Cell*, 47: 929-937 (1986).
Stetler & Thorner, *Proc. Natl. Acad. Sci. USA* 81: 1144-1148 (1984).
Trueheart et al., *Molecular and Cellular Biology* 7: 2316-2328 (1987).
Roeder & Fink, *Cell*, 21: 239-249 (1980).
Bulawa et al., *Cell*, 46: 213-225 (1986).
Trueheart & Fink, *Yeast*, 2: S394 (1986).
Van Arsdell et al., *Molecular and Cellular Biol.*, 7(2): 749-759 (1987).
McCaffrey et al., *Chem Abstracts*, 197: No. 128287U.
Nonato & Shishido, *Chem. Abstract*, 108: No. 217221f.
Miyajima et al., *Chemical Abstract*, 103: No. 208060X.
Vlasuk et al., *Chemical Abstracts*, 104: No. 220092n.
Singh et al., *Chemical Abstract*, 104: No. 16037u.

*Primary Examiner*—Robin L. Teskin
*Assistant Examiner*—Richard C. Peet
*Attorney, Agent, or Firm*—Hamilton, Brook, Smith & Reynolds

[57] ABSTRACT

A yeast promoter inducible by the appropriate pheromone and a method of expressing a gene of interest in substantial quantities by placing it under the control of the inducible promoter. DNA encoding a protein of interest is fused or linked to a pheromone - inducible yeast promoter, such as the FUSI or the FUS2 promoter, and the fusion is inserted onto a high copy vector; the resulting product is introduced into wild type yeast cells. Stimulation of these yeast cells by the appropriate pheromone results in induction of transcription of the yeast promoter and expression of the protein of interest in substantial quantities.

33 Claims, 14 Drawing Sheets

FIG. 4

```
1   TATTAGAGTCAGTTCGACTGCCTAGAAGAACTGCTGGTTGTCAGGATTGTGATGGGGCATTCGCTGTGTATTATGACCATCGTGTATTGCAATGCTCACCACTGTGTCTTCCTGCCGT       120
                                                                                                       EndPhePheGlnGlnAsnAspProCysHisProAlaThr
    ATAATCTCAGTCAAGCTGACGGATCTTCTGACGACCAACAGTCCTAACACTACCCCCGTAAGACGACATAACTGGGTAGCATAGCGTTACGAGTGGTGACAACAGAAGGACGGCA
    EndPhePheGlnGlnAsnAspProCysGluAlaThrAsnHisGlyMetThrAspCysHisGluCysTrpGlnArgGlyAlaThr

121 GGTATCGACTGGTGGTGCAGGGGGTGCAAAATTGGCAACGATTCCACGCGTCGTTTGTGCTTGAGCCTGTTCCAAGTGTTTGATTTTTCATTAGCCTCTTCAAGTTTTTCGTTAAGGATGC       240
    GlyTyrArgLeuValValAlaAlaLeuGlnGlySerValGlnAsnTrpGlnArgPheProArgValValCysLeuSerLeuPheGlnValLeuIlePheHisSerLeuGlnValPheValArgMet
    CCATAGCTGACCACGTCCCCCAGCTTTAACCGTTGCAAGGTGCCGACAAGAAGTAATGACAAACTGGACAGGACTTGGACAAGAAGTTGACAAACTAAAAAAGTAATGACAAACTACG
    ThrAspValProAlaProProAspPheIleProLeuSerGluValAlaAlaThrGlnAlaGlnAlaGlyLeuGluLeuLysGlnAlaGlnAlaGlnLeuLysIleLysGluAsnAlaGlyLeuLeuLysIleLysThrLeuSerAla

241 CACCTCTTCCGATGAGGAATCTGTGGTTTTGTCAAAATAGTCCTGCTCAAATTTGGTATCTTACTGAGCGAATCGTTATGCATTTCAATGTTCGCTTCTTTAGCCACTT       360
    HisLeuPheArgEndGluSerValValLeuSerLysEndSerLeuLeuLysLeuValIleLeuLeuThrGluArgIleValMetHisPheAsnValArgPheLeuSerHis
    GTGGAGAAGGCTACTCCTTAGAACACCAAAACAGTTTTATCAAGGAACCAGAGTTAAAACCATAAGAAATGACTCCTTAGCATACGTAAAAGTTAACAAGCGCAAGAAATCGGGTGAA
    ValGluGluSerSerAspGlnProLysPheLeuLeuValPheGluLysSerLeuAsnGlnTyrGluLeuLysSerLeuAsnAspAsnHisMetLeuGlnLeuArgGluAlaTrpLys

361 TGTCTTGTGTAACTCAAATTGGTCTCTATGTGCTAATTGTTCCAGGAGTTCGACATCTCGTTGGCACCAGTCTGTTTTTCAGGAGTGGGTGATTATGAAAGATTTCTCTTCGTT       480
    CysLeuCysAsnSerAsnTrpSerLeuMetCysEndLeuGlnValSerThrSerValGlyThrSerLeuPheSerGlyGlyEndLeuEndArgPheLeuPheVal
    ACAGAACACATTGAGTTTAACCAGAAGAGAATAACAACGGATTAACAGGTCGACAAAAAGTCCTCAAGGTCGAGAGCAACCGTGGTCACCAACTAACTATACTCTTTCTAAAGAGAAGCAA
    ThrLysHisLeuGluPheGlnAspGlnLeuAsnArgLeuGlnLeuGlnValLeuLeuGlnLysLysLeuLeuValAspGlnAsnAlaGlyThrProGlnAsnHisSerLeuAsnArgGluGluAsn

481 TTCTTTGATCTTCTTCGTAGTTGGCTTACGACAAGTAGCTGTCATTCTCAGCGTCAAAAAACTGCTTTGTTTGGCTGTCGTCCAGCTCCAATTGTTGCTTGAGATG       600
    PhePheAspLeuLeuValValGlyLeuArgGlnValAlaValIleLeuSerValLysAsnCysPheValTrpLeuSerSerSerAsnCysCysLeuArgMet
    AAGAACTAGAAGAAGCACATCAACCGAATCGTCGTTCATCGACAAGTAAGAGTCGACAGTTTTTGACGAAAAACAAGACGCAAGCCAAGCTCGAGGTTAACAACGAACTCTAC
    GluLysIleGluGluHisGlnSerValValAlaLeuLeuGlnGlnAsnGluAlaAspPhePheGlnLysGlnAlaGlnArgArgGluLeuGluLeuGlnLysGlnLysLeuHis
```

FIG. 4 CONT.

```
601 GTCTATCTCTTCTCTCTTCTGTATTGGCTTCATACCTATCAAAGTCGGTTGCACTTCTTCTGAGGACCATTCTTTGGTCATCGAGTAGCCTTTGTAGTGTAGTGTTCCTTTG  720
    CAGATAGAAGAAGAGAAGAAGAACATAACACCGAAGTATGGAATAGTTTCAGCAAGTCCTGGTAAGAACCAGTAGCTCATCGAGAAAACATCACATCAACAAAGGAAAC
    AspIleGluLysArgGluGlnIleThrAlaGluTyrArgAspPheThrProGlnValGluGluLeuValMetArgGlnAspLeuLeuArgLysTyrHisLeuGlnLysArgGln

721 TAGCTTTTCGATGGTCAATTGGGCTTCTCGTAATTCAATTCATGTAACTTCCGCTGCTATTGAGGTCATTCATGTGCCATTGTCCGGTTCCAATCGCTGGTGGTGTTGTGATTAGCCTTCT  840
    ATCGAAAAGCTACCAGTAACCGAAGAGCATTAAGTGAAGCGACGATAACTCCAGTAGTAACAGGCCAAAGGTTACGACCACCACAACACTAATCGGAAAGA
    LeuLysGluIleThrLeuGlnAlaGluArgLeuGlnIleThrValGluSerSerAsnMetHisGlyAsnAspProLysTrpAspSerThrThrAsnHisAsnAlaLysArg

841 GTCTGATGACAGGATAGAGTCCACCTCCATTCGTCTCCTGTATCGTAACCAAATTCTTGCTGTTGATGATCCGATGCCTCCTGGTCCATCGACTGTTGATTACCGCTGTGCCG  960
    CAGACTACTGTCCTATCCAGCTGGAGGTAAGACAGAAGACATAGCATTGGTTTAAGAACGACATAGCAGGAGACCAGGTAGCTGACAACTAATGGCGACACGGC
    AspSerSerLeuIleSerAspVaIGluMetArgAsnAspTyrGlyPheGluGlnGlnHisHisAspSerAlaGluGlnAspMetSerGlnAsnGlySerHisArg

961 ACTGGTGATCCGGAAACTTCTCATGGTGTGGGGATTAGGATCATCCATGGAGAGAACTGGTAGTGAGCCTCACATAGATCTGTTTTTGGGTATTGATAGCGGTTCCATTGTCGT  1080
    TGACCACTAGGCCTTTGAAGAGTAGCCACACCCCCTAATCCTAGTAGGCTAGTAGGACCCTCTTGACCAATCATACTAGACAAAAACCATACTCGCCAAGTAACAGCA
    SerThrIleArgPheSerArgMetProThrProSerLysProAspAspMetProSerPheGlnAsnThrLeuArgValIleSerArgAsnLysProIleSerLeuProMetThrThr

1081 TCTTCTCGAGGTTTGCGATATCGATGCCTTCTCGATCAATGATGAGGACTTTTGCAACTGAATAATAGTCCACTTTGAGGATACTCCGTTGAAAATACTTCTTCCCATGAATGATCC  1200
     AGAAGAGCTCCAAACGCTATAGCTACTACGGAAGACTAGTTACTACGCTGAAAAACGTTGACTTATTTATCAGGTGAACTCCTATGAGGCAAACTTTATGAAGAAGGGTACTACTAGG
     ArgArgSerThrGlnSerIleSerAlaValLysGluIleLeuGlnIleLysPheLeuGlnSerGlnProTyrGluThrGlnPheTyrLysGlyMetPheSerGly
```

FIG. 4 CONT.

```
1201 ATCGTTCTTACCAATGTTGGCAAGTAAGTCTACACCAGTAAGTTCCAGCTTCGTGTCCACTGGACCCACGTATTTCAGTTGTCCGGCGCCCAAATTTGGGATTTGTATGAAACATCC  1320
     AspAsnLysGlyIleAsnAlaLeuLeuAspValGlyAlaPheMetGlyAlaLysThrAspValProGlyValTyrLysLeuGlnGlyArgGlyLeuAsnProIleGlnIlePheCysGly
     TAGCAAGAATGGTTACAACCGTTCATTCAGATGTCGTTTGTAAGGTCGAAAGCACAGGTGACCTGGGTGCATAAAGTCAACAGGCGCGGGGGTTTAAACCCTAAACATACTTTGTAGG
1321 TATCTTTCTTTGATATCTATCCATGGTATTTCAAACGACATACACAGCCAGCCACAGCTCAACGCCTTTACCTGTCCTTTGATGCCTGCTCGTCCAAACGTTTTTGGTGTCTTGGCCA  1440
     IleLysArgGlnTyrArgAspMet ──BIK 1
     ATAGAAAGAAAACTATAGAGGTA
1441 ATTGCCCTTCTGAAAAATCTCACTGTCCGCAACTCATTAAAAGATACCCAAGCAAGCTACGATAAAAGAAGGAGAAAGTTCATTAAAAGAACGTACATATAGGATACAAACGTATAG   1560
     MetAspThrAspLysLeuIleSerGluAlaGlySerHisPheSerGlnGlyAsnHisAlaGluAlaValAlaAlaLysLeuThrSerAlaAlaGlnSerAsnProAsnAsp
1561 CAAAGATCTGAATGGATACGGATAAGTTAATCTCAGAGAGGCTGAGTCTCATTTTTCAAGGAAACATGGAGAGCTGTGCCGAAGTTGACATCCGCAGCTCAGTCGAACCCAATGAC   1680
     GluGlnMetSerThrIleGluSerLeuIleGlnLysIleAlaGlyTyrValMetAspAsnArgSerGlyGlySerAspAlaSerGlnAspArgAlaAlaGlyAlaGlyGlySerPheMet
1681 GAGCAAATGTCAACTATTGAATCATTAATTCAAAAAATCGCAGGATACGTCATGGACAATCGTAGTGGCGGCTCCGACAATCGTCGCTGCTGTGGTGGTTCATCTTTTATG         1800
     AsnThrLeuMetAlaAspSerLysGlySerMetGlyAlaSerGlyLeuAlaLeuAlaSerGlyPhePheLysSerGlnPheAsnAsnSerGlnGlyGlnGly
1801 AACACTTTAATGGCAGACTCTAAGGGTTCTTGCCACAGTAGCTTGTTAGCAGTGATGACACACTCATCAAATAAAGTTCTTCTAACAGAGGGTTTGACGTA                    1920
     GlyThrValMetSerMetLeuSerGlyMetGlyAlaSerGlyGlyGlySerGlyGlyGlySerGlyGlnSerGlnGlyAsnAsnSerGlnGlyGlnGly
1921 GGGACTGTCATGTCAATGCTAAGTGGTTCTGGCGGCGGAAGTATGGGTCCGGGCGGCGGAGCCAAAGTATGGGTGCTTCCGGGTTCCAATTCTTTAAGTCAGGTAACAATTCCAAGGTCAGGA  2040
```

FIG. 4 CONT.

```
2041 CAAGGTCAAGGTCAAGGTCAAGGACAAGGTCAAGGTTCTTTTACTGTTCTTTAACTTCATCTTCATGATTCCAACAACAATAATCAGGAGGTCAAAAT 2160
     GlnGlyGlnGlyGlnGlyGlnGlyGlnGlyGlnGlyGlnGlySerPheThrAlaLeuAlaSerLeuThrSerSerPheMetAsnSerAsnAsnGlnGlyGlnAsn

2161 CAAAGCTCCGGTGGTTCCTCCTTTGGAGCACTGGCTTCTCTATGGCCAAGCTCTTTTATGCATTCAATAATAATCAGAACTCCAACAATAGTCAACAGGGCTATAACCAATCCATCAAAAC 2280
     GlnSerSerGlyGlySerPheGlyGlySerMetAlaSerMetAlaLeuAlaSerMetAlaSerPheMetHisSerAsnSerAsnAsnSerGlnGlnGlyTyrAsnGlnSerTyrGlnAsn

2281 GGTAACCAAAATAGTCAAGGTTACAATAATCAACAGGTGGCAACGGTACCAACAAGGTACCAACAACAACAGGACAATCTGGTGGTCTTTTTCCTCATTGGCCTCCATGGCTCAATCT 2400
     GlyAsnGlnAsnSerGlnGlyTyrAsnAsnGlnGlnGlyGlyAsnGlyTyrGlnGlnGlySerGlyGlyAlaPheSerSerLeuAlaSerMetAlaGlnSer

2401 TACTTAGGTGGTGGACAAACTCAATCAACAACAGCAATAACAACAAGGCCAAAACAACAGCAATACCAGCAATCATCAGCATCAACAACAGGTCAGCAG 2520
     TyrLeuGlyGlyGlyGlnThrGlnSerAsnGlnThrGlnGlnAsnGlnGlnGlnGlyGlnAsnGlnGlnTyrGlnGlnGlyGlnHisGlnGlnGlnGlnGln

2521 CAGCAACAAGGCCACTCAGTTCATTCTCAGTTTGGCTTCCATGGCAAGTTCCTACCTGGGCAATAACTCCAATTCAAATTCGAGTTGAGATTTCGAGAATCTCCATTCAAATTCGAGTTGCGGGCCAGCAACAGGTTATGGGGGCCAGCAACAGGGCTAATGAGTAGTATGGTA 2640
     GlnGlnGlnGlyHisSerValHisSerGlnLeuTrpLeuProTrpGlnValProIleGlnIleArgValMetGlyAlaSerAsnArgLeuMetSerMetVal

2641 GACCGCAACAGAATGGTCAACAGCAATCCAATGAGTACGGAAGACCGAAGACCGAATACGGGAACACCTCCAATCCTTCATTTTCTGGCAACTTTCTCAACAGA 2760
     AspArgAsnArgMetValAsnSerAsnProMetSerThrGluAspArgAsnThrAlaGluThrArgThrProMetAspSerProSerIlePheLeuAlaThrPheLeuAsnArg

2761 ACAATAACGGCAACCAGAACCGCTACTGAACGATGATTCAGTTCGCCTTCGCCTTCTATCCTTTGTTACGTATTGTTTACGTATTGTTTATATATAACTTATTTTTTTTTTATTAATTGGGTGCAAGACAAT 2880
     ThrIleThrAlaThrArgThrAlaThrGluArgEnd

2881 TTTGTTGTCAGTGATGCCTCAATCCTTCTTTGCTTCCATATTTACCATGTGGACCCTTTCAAAACAGAGTGTATCTGCAGGATGCCCTTTTGACGTATTGAATGGCATAATTGC 2999
```

FIG. 4 CONT.'

```
3000 ACTGTCACTTTTCGCGGTCTGTCTCATTTGGTGCCATGATGATGAAACATGAAACGTCTGTAATTCTGGGATTGGTTTATTTAAATGACAATGTAAGAG 3119

3120 TGGCTTTGTAAGGTATGTGTGCTCTTAAAATATTTGGATACGACATCCTTTATCTTTTTTTCCTTTAAGAGCAGGATATAAGCCATCAAAATGTAGCAACAATA 3239
                                                                             FUS 1 ──► MetValAlaThrIle

3240 ATGCAGACGACAACAACTGTGCTGACGACAGTGCCCGACGAGTGCCGAGTGTAACAGTGTAACAGTAACAGACAATAGCG 3359
   6 MetGlnThrThrThrValLeuThrThrValAlaAlaMetSerThrLeuAlaSerSerAsnTyrIleSerSerGlnAlaSerSerValThrThrValThrIleAla

3360 ACATCAATACGCTCTACACCGTCTAATCTACTCTTTCTAATGTGGGGCTCAGCCAAAATCATCTCAGCAAGCACAATTGGGCTTCAATGGACTCCATCGGAATATTCTGTTC 3479
  46 ThrSerIleArgSerAsnLeuLeuPheSerArgSerAlaAlaGlnProLysSerSerAlaSerThrIleGlyLeuSerIleGlyIleLeuProIleGlyIleLeuPheCysPhe

3480 GGATTACTATCCTTTGTGTTATTTCTACCTTAAAAGGAATTCGGTGTCCATTCAATCCACCATGCAGTCTACGATTCCAAGGGAAGAGGAATATTGTGCCGCACTAATTGGTTC 3599
  86 GlyLeuLeuLeuLeuCysTyrPheTyrLeuLysArgAsnSerValSerIleSerAsnProProMetSerAlaThrIleProArgGluGluGluTyrCysArgArgThrAsnTrpPhe

3600 TCACGGTTATTTTGGCAGAGTAAGTGTGAGGATCAGAATTCATATATCTAATCGTGATATATTGAGAAGTATAACGACCTCGGGTGATAACATGTCTTCAAAAATACAGTAC 3719
 126 SerArgLeuPheTrpGlnSerLysCysGluAspGlnAsnSerTyrSerAsnArgAspIleGluLysTyrAsnAspThrGlnTrpThrSerGlyAspAsnMetSerSerLysIleGlnTyr

3720 AAAATTTCCAAACCCATAATACGCAGCAGATACTGACACCTAAGAAAACGTGAAGAACCCATATGCTTGGTCTGTAAAAACATTTCGTAGACCCCAAAGTGAACGAAATGGAGGAA 3839
 166 LysIleSerLysProIleIleProGlnHisIleLeuThrProLysLysAsnProTyrAlaTrpSerGlyLysAsnLeuSerLeuAspProTyrAlaTrpSerGlyLysAsnLeuSerLeuAspProLysValLysAsnGluMetGluGlu
```

FIG. 4 CONT.

```
3840 GAGAAAGTTGTGGATGCATTCCTGTATACTAACCACCGAATATGTCCATATGAATTACCTTCTCAAAAACGGTGTCCTCAAAGAAACTGCG 3959
 206 GluLysValValAspAlaPheLeuTyrThrLysProProAsnIleValHisIleGluSerSerMetProSerTyrAsnAspLeuProSerGlnLysThrValSerLysThrAla

3960 TTAAAAACGAGTGAGAAATGGAGTTACGAATCTCCACTATCTCGATGGTCTTGAGGGTTCTACATACTTTAAGGATTATGGCTTATCAAAGACCTCTTTAAAGACCCCAACTGGGCT 4079
 246 LeuLysThrSerGluLysTrpSerTyrGluSerProLeuSerArgTrpSerSerTyrPheLysAspTyrGlyLeuSerLysThrSerLeuLysThrProThrGlyAla

4080 CCACAACTGAAGCACAAATGAAAATGCTCTCCGATAAGGGTTACTTCAATGAGTCAGATATAATGCTGACGAACCATGCCCATCTTGGAGTATAATAACACGCCTCTGGATGCA 4199
 286 ProGlnLeuLysGlnMetLysMetLeuSerArgIleSerLysGlyTyrPheAsnGluSerAspIleMetProAspGluArgSerProIleLeuGluTyrAsnAsnThrProLeuAspAla

4200 AATGACAGTGAATAACTTGGTAATACCGCCAGATTCACAATCACATCTTATCGCAACAATAACATCGATCATCACTCAGTCGATATACGGTACTACTGCA 4319
 326 AsnAspSerValAsnAsnLeuGlyAsnThrThrProAspSerGlnIleThrSerTyrArgAsnAsnAsnIleThrAlaArgProHisSerValIleTyrGlyThrThrAla

4320 CAACAAACTTTGGAACCAACTTCAATGATCATCATGACGAATAAAAGACCGAGTTGATAATCCACCCATCTAAAGAAGGAAAAAGAAGACAA 4439
 366 GlnGlnThrLeuGluProThrSerAsnAspHisHisAspCysAsnLysSerThrGluLysHisGluLeuIleProThrProSerLysProLeuLysLysArgLysArgGln

4440 AGTAAAATGTATCAGCATTTACAACACATTGTCACGTTCTAAACCATTGCCGCTTACTGCCCTTACTGCCGTCCAATTAGGAGGAGACATATACAGTTATTCAG 4559
 406 SerLysMetTyrGlnHisLeuGlnHisLeuSerArgSerProLeuProLeuProThrProAsnSerLysTyrAsnGlyLeuLysThrTyrThrValIleGln

4560 GATTACGAGCTAGATTGACAGACGAAATAAGAATTCGCTGGGTGAAAAGTAAAATTCGGCCACTCATACCATGGATGGTGTCTGTAGAAAAGTGTAATACACAAAGGGTTCT 4679
 446 AspTyrGluProArgLeuThrAspGluIleArgIleSerLeuGlyIleGluLysValLysIleLeuAlaThrHisThrArgAspGlyTrpCysLeuValGluLysCysAsnThrGlnLysGlySer

4680 ATTCACGTCAGTGTGACGATAAAAGATACCTCCAAGAAATACGACTGATGAAAATAATATTGACGTTGCCATTTAATCTATACC 4799
 486 IleHisValSerAspAspLysSerArgTyrLeuAsnGluAspCysArgGlyIleValProGlyAspCysLeuGlnGluTyrAspEndEnd    End    End
```

FIGURE 5

```
    GATCTTTGAATTTTGCATTAAACAGTGAAGAAGGTAGTAGAGACCGTTTCAAAGTCATA
1   ------------+----------+----------+----------+----------+----------+   60
    CTAGAAAACTTAAAACGTAATTTGTCACTTCTTCCATCATCTCTGGCAAAGTTTCAGTAT
              10         30         50
```

```
    ACAGAGTTTTAGGTAGAGGTGCCATCAGTTATTCTGACATCACTATTTAATGATGGATC
61  ------------+----------+----------+----------+----------+----------+   120
    TGTCTCAAAAATCCATCTCCACGGTAGTCAATAAGACTGTAGTGATAAATTACTACCTAG
              70         90        110
```

```
    ATAACGATCTATTGTGCCCGCCGCGTCACAAATGCGCCCCGAACTTGTCGCGAAGTTAAT
121 ------------+----------+----------+----------+----------+----------+   180
    TATTGCTAGATAACACGGGCGGCGCAGTGTTTACGCGGGGCTTGAACAGCGCTTCAATTA
             130        150        170
```

```
    CTGAAACATATATGTTACCTACTGAAACAGCGCATGTTGGAAAAGACAAAGGTGAAGACG
181 ------------+----------+----------+----------+----------+----------+   240
    GACTTTGTATATACAATGGATGACTTTGTCGCGTACAACCTTTTCTGTTTCCACTTCTGC
             190        210        230
```

```
    AAGTTGTATATTTAAGATAGACCCTTTATACATCCTTTTGAAAAAATTATTAATGTGGCA
241 ------------+----------+----------+----------+----------+----------+   300
    TTCAACATATAAATTCTATCTGGGAAATATGTAGGAAAACTTTTTAATAATTACACCGT
             250        270        290
```

```
    ACCGTCTTTTATTTGACAAAGTATCTTTTTTCTTTGTGAAACCAATTTTAGGTTTTCTTG
301 ------------+----------+----------+----------+----------+----------+   360
    TGGCAGAAAATAAACTGTTTCATAGAAAAAGAAACACTTTGGTTAAAATCCAAAAGAAC
             310        330        350
```

MetPheLysThrSerTyr
```
    TTATAGTAAGTTCTTAAGAAAAAGACAAGAAAACCCCTTGCGATGTTTAAGACTTCATAT
361 ------------+----------+----------+----------+----------+----------+   420
    AATATCATTCAAGAATTCTTTTTCTGTTCTTTTGGGGAACGCTACAAATTCTGAAGTATA
             370        390        410
```

AsnLeuTyrAspLeuAsnTyrProLysAsnAspSerLeuThrProIleArgAspTyrLys
```
    AACTTGTACGATTTGAACTATCCGAAAAATGATTCATTAACGCCAATAAGAGACTACAAA
421 ------------+----------+----------+----------+----------+----------+   480
    TTGAACATGCTAAACTTGATAGGCTTTTTACTAAGTAATTGCGGTTATTCTCTGATGTTT
             430        450        470
```

AsnAspTyrPheHisLysAsnAspAspLysLeuProGluIleValArgLysProThrArg
```
    AATGACTATTTTCATAAAAATGATGACAAATTACCAGAAATTGTTAGAAAACCTACGAGA
481 ------------+----------+----------+----------+----------+----------+   540
```

FIGURE 5 (CONT'D)

```
            LysLeuSerLysHisGluAsnLysLeuAsnAspLysLysPheThrAsnLysArgProAla

AAGTTATCGAAACATGAAAACAAACTCAACGATAAAAAATTCACGAATAAACGACCAGCA
541    ------------+----------+----------+----------+----------+----------+  600
       TTCAATAGCTTTGTACTTTTGTTTGAGTTGCTATTTTTTAAGTGCTTATTTGCTGGTCGT
                550                570                590

SerLeuAspLeuHisSerIleValGluSerLeuSerAsnLysLysIleTyrSerProIle

AGTCTGGACTTGCATTCTATAGTGGAGAGCCTGAGCAATAAAAAAATTTACTCTCCTATT
601    ------------+----------+----------+----------+----------+----------+  660
       TCAGACCTGAACGTAAGATATCACCTCTCGGACTCGTTATTTTTTAAATGAGAGGATAA
                610                630                650

AsnThrGluIlePheGlnAsnValValArgLeuAsnLeuSerProGlnIleProAsnSer

AACACAGAGATATTTCAAAATGTCGTGAGACTGAATTTGAGCCCTCAGATTCCCAATTCT
661    ------------+----------+----------+----------+----------+----------+  720
       TTGTGTCTCTATAAAGTTTTACAGCACTCTGACTTAAACTCGGGAGTCTAAGGGTTAAGA
                670                690                710

ProHisGluGlyCysLysPheTyrLysIleValGlnGluPheTyrLeuSerGluValGlu

CCTCACGAGGGATGCAAATTTTATAAAATCGTACAGGAGTTTTACCTCTCTGAAGTGGAA
721    ------------+----------+----------+----------+----------+----------+  780
       GGAGTGCTCCCTACGTTTAAAATATTTTAGCATGTCCTCAAAATGGAGAGACTTCACCTT
                730                750                770

TyrTyrAsnAsnLeuLeuThrAlaAsnAsnValTyrArgLysAlaLeuAsnSerAspPro

TATTACAATAATTTGTTAACCGCAAATAACGTATACAGAAAGGCATTGAATAGTGATCCA
781    ------------+----------+----------+----------+----------+----------+  840
       ATAATGTTATTAAACAATTGGCGTTTATTGCATATGTCTTTCCGTAACTTATCACTAGGT
                790                810                830

ArgPheLysAsnLysLeuValLysLeuAspSerSerAspGluLeuLeuLeuPheGlyAsn

AGATTCAAGAATAAACTTGTCAAGCTTGATTCAAGTGACGAGCTATTGCTTTTTGGGAAC
841    ------------+----------+----------+----------+----------+----------+  900
       TCTAAGTTCTTATTTGAACAGTTCGAACTAAGTTCACTGCTCGATAACGAAAAACCCTTG
                850                870                890

IleAspThrIleAlaSerIleSerLysIleLeuValThrAlaIleLysAspLeuArgLeu

ATTGACACTATTGCGTCAATCAGCAAAATACTGGTAACGGCAATAAAAGACCTACGGTTA
901    ------------+----------+----------+----------+----------+----------+  960
       TAACTGTGATAACGCAGTTAGTCGTTTTATGACCATTGCCGTTATTTTCTGGATGCCAAT
                910                930                950

AlaLysGlnArgGlyLysMetLeuAspAlaAsnGluTrpGlnLysIleLeuThrLysAsn

GCCAAGCAACGTGGGAAAATGTTGGATGCGAATGAATGGCAAAAGATATTGACCAAAAAT
961    ------------+----------+----------+----------+----------+----------+ 1020
       CGGTTCGTTGCACCCTTTTACAACCTACGCTTACTTACCGTTTTCTATAACTGGTTTTTA
                970                990                1010
```

FIGURE 5 (CONT'D)

```
                GluValGlnGlnGlnLeuTyrSerThrPheAspIleSerGluAlaPheGluGlnHisLeu
        GAGGTACAACAGCAGCTATATTCAACTTTTGATATTTCAGAGGCGTTCGAGCAACATTTG
1021    ----------+----------+----------+----------+----------+----------+    1080
        CTCCATGTTGTCGTCGATATAAGTTGAAAACTATAAAGTCTCCGCAAGCTCGTTGTAAAC
                  1030       1050       1070

LeuArgIleLysSerThrTyrThrSerTyrPheValSerHisGlnLysGlnMetGluLeu
        TTAAGAATCAAATCCACCTACACAAGCTATTTTGTTAGCCACCAAAAACAAATGGAACTA
1081    ----------+----------+----------+----------+----------+----------+    1140
        AATTCTTAGTTTAGGTGGATGTGTTCGATAAAACAATCGGTGGTTTTTGTTTACCTTGAT
                  1090       1110       1130

PheThrThrLeuArgMetAsnLysAsnHisPhePheAsnLysTrpTyrGluTyrCysLeu
        TTTACTACATTAAGGATGAATAAGAATCATTTTTTTAACAAGTGGTATGAATATTGTTTA
1141    ----------+----------+----------+----------+----------+----------+    1200
        AAATGATGTAATTCCTACTTATTCTTAGTAAAAAAATTGTTCACCATACTTATAACAAAT
                  1150       1170       1190

LysGluSerGlyCysIleLysLeuGluAspIleLeuLysSerProMetLysArgLeuThr
        AAAGAGAGTGGATGTATAAAGTTAGAGGACATATTGAAAAGCCCGATGAAAAGACTGACT
1201    ----------+----------+----------+----------+----------+----------+    1260
        TTTCTCTCACCTACATATTTCAATCTCCTGTATAACTTTTCGGGCTACTTTTCTGACTGA
                  1210       1230       1250

GlnTrpIleAspThrLeuGluThrLeuGluSerCysTyrGluAspIleLeuSerProGlu
        CAGTGGATTGATACTTTGGAAACTTTGGAAAGCTGTTACGAAGATATTCTTTCGCCAGAA
1261    ----------+----------+----------+----------+----------+----------+    1320
        GTCACCTAACTATGAAACCTTTGAAACCTTTCGACAATGCTTCTATAAGAAAGCGGTCTT
                  1270       1290       1310

LeuGlyLeuLysLeuSerProThrArgArgLysTyrSerLeuPheSerAsnLysLeuGlu
        TTGGGCTTGAAACTAAGCCCGACAAGAAGAAAATATTCTTTATTTTCCAATAAGTTAGAA
1321    ----------+----------+----------+----------+----------+----------+    1380
        AACCCGAACTTTGATTCGGGCTGTTCTTCTTTTATAAGAAATAAAAGGTTATTCAATCTT
                  1330       1350       1370

ThrGluValSerGluTyrLysSerAsnSerMetTyrAsnPheSerLeuThrProSerGlu
        ACCGAGGTCTCCGAGTATAAGAGTAATTCCATGTATAATTTCAGTTTAACCCCATCAGAG
1381    ----------+----------+----------+----------+----------+----------+    1440
        TGGCTCCAGAGGCTCATATTCTCATTAAGGTACATATTAAAGTCAAATTGGGGTAGTCTC
                  1390       1410       1430

IleIleGlnSerTyrAspGluAspGlnPheThrHisLeuLeuLysProProAspLysGln
        ATTATACAAAGTTATGATGAAGATCAGTTTACACACCTTTTAAAACCCCCAGACAAACAA
1441    ----------+----------+----------+----------+----------+----------+    1500
        TAATATGTTTCAATACTACTTCTAGTCAAATGTGTGGAAAATTTTGGGGGTCTGTTTGTT
                  1450       1470       1490
```

FIGURE 5 (CONT'D)

```
       AATAAAAATATATGTAATGCATCTCGACAAGAGAGTAATTTGGATAATAGTAGAGTTCCT
1501   ----------+----------+----------+----------+----------+----------+  1560
       TTATTTTTATATACATTACGTAGAGCTGTTCTCTCATTAAACCTATTATCATCTCAAGGA
                 1510           1530           1550

SerLeuLeuSerGlySerSerSerTyrTyrSerAspValSerGlyLeuGluIleValThr
       TCTCTTCTTTCTGGATCATCGAGTTACTACTCAGATGTATCAGGGCTAGAAATTGTCACT
1561   ----------+----------+----------+----------+----------+----------+  1620
       AGAGAAGAAAGACCTAGTAGCTCAATGATGAGTCTACATAGTCCCGATCTTTAACAGTGA
                 1570           1590           1610

AsnThrSerThrAlaSerAlaGluMetIleAsnLeuLysMetAspGluGluThrGluPhe
       AATACTTCAACTGCCTCAGCTGAGATGATAAATCTAAAAATGGATGAAGAAACAGAATTT
1621   ----------+----------+----------+----------+----------+----------+  1680
       TTATGAAGTTGACGGAGTCGACTCTACTATTTAGATTTTTACCTACTTCTTTGTCTTAAA
                 1630           1650           1670

PheThrLeuAlaAspHisIleSerLysPheLysLysValMetLysGlyLeuLeuGluLeu
       TTTACATTGGCAGATCACATCAGTAAATTCAAGAAAGTAATGAAAGGTTTGTTAGAATTA
1681   ----------+----------+----------+----------+----------+----------+  1740
       AAATGTAACCGTCTAGTGTAGTCATTTAAGTTCTTTCATTACTTTCCAAACAATCTTAAT
                 1690           1710           1730

LysLysAsnLeuLeuLysAsnAspLeuSerGlyIleIleAspIleSerLeuArgArgIle
       AAAAAGAATTTATTGAAAAACGATCTGTCAGGCATTATTGATATCAGTTTAAGAAGAATA
1741   ----------+----------+----------+----------+----------+----------+  1800
       TTTTTCTTAAATAACTTTTTGCTAGACAGTCCGTAATAACTATAGTCAAATTCTTCTTAT
                 1750           1770           1790

AsnAlaTrpLysLysValIleGluCysGluArgProSerGlyAlaPhePheAlaHisAsp
       AATGCATGGAAAAAGGTGATCGAGTGCGAACGCCCTTCTGGTGCATTTTTTGCGCACGAT
1801   ----------+----------+----------+----------+----------+----------+  1860
       TTACGTACCTTTTTCCACTAGCTCACGCTTGCGGGAAGACCACGTAAAAAACGCGTGCTA
                 1810           1830           1850

AsnLeuIleSerThrMetCysSerSerTyrIleAspLysLeuHisGluGlnLysAsnGln
       AACTTAATATCGACCATGTGTTCTTCGTACATAGATAAACTGCATGAACAAAAAAATCAA
1861   ----------+----------+----------+----------+----------+----------+  1920
       TTGAATTATAGCTGGTACACAAGAAGCATGTATCTATTTGACGTACTTGTTTTTTTAGTT
                 1870           1890           1910

ValThrIleLeuLysLeuThrGluLeuGluThrAspValMetAsnProLeuGluArgIle
       GTAACAATTTTGAAACTCACAGAGCTCGAAACAGATGTGATGAACCCACTTGAAAGAATC
1921   ----------+----------+----------+----------+----------+----------+  1980
       CATTGTTAAAACTTTGAGTGTCTCGAGCTTTGTCTACACTACTTGGGTGAACTTTCTTAG
                 1930           1950           1970

IleAlaHisCysThrThrValLysSerLysLeuLysAspLeuGlnAlaTyrMetLeuPhe
```

FIGURE 5 (CONT'D)

```
     TATCGGGTAACATGATGGCAATTTTCGTTTGATTTTCTAAACGTTCGAATGTACAATAAA
           1990                2010                2030

LeuGlnGluLysLysAlaAsnValArgAspIleLysArgAspLeuLeuGlyMetHisPhe
     TTACAAGAAAAAAAAGCAAATGTGCGAGATATTAAACGTGACTTGTTGGGAATGCATTTC
2041 ----------+----------+----------+----------+----------+----------+ 2100
     AATGTTCTTTTTTTTCGTTTACACGCTCTATAATTTGCACTGAACAACCCTTACGTAAAG
           2050                2070                2090

GlnAsnLeuGlnAsnGlnMetLysArgGluLeuProValPheIleThrLeuIleProArg
     CAAAACCTGCAAAACCAGATGAAAAGGGAATTACCGGTCTTTATTACTTTGATCCCACGA
2101 ----------+----------+----------+----------+----------+----------+ 2160
     GTTTTGGACGTTTTGGTCTACTTTTCCCTTAATGGCCAGAAATAATGAAACTAGGGTGCT
           2110                2130                2150

TyrTyrArgMetTyrLeuValGluLeuTyrGlnSerLeuLeuLysIlePheGlyAsnHis
     TACTATCGAATGTATCTTGTTGAACTATATCAAAGTCTTCTTAAAATATTTGGAAATCAT
2161 ----------+----------+----------+----------+----------+----------+ 2220
     ATGATAGCTTACATAGAACAACTTGATATAGTTTCAGAAGAATTTTATAAACCTTTAGTA
           2170                2190                2210

CysTrpTrpLysLysIleProAlaLysArgSer
     TGCTGGTGGAAAAAAATACCTGCAAAAAGATCTTGAAAATATGTCTCTTAATGACTCTAT
2221 ----------+----------+----------+----------+----------+----------+ 2280
     ACGACCACCTTTTTTTATGGACGTTTTTCTAGAACTTTTATACAGAGAATTACTGAGATA
           2230                2250                2270

AGCTACCGGCCAAATTAAAAATCTTGATATTTTGCAGTGTTATTCTAAATCACGATATAT
2281 ----------+----------+----------+----------+----------+----------+ 2340
     TCGATGGCCGGTTTAATTTTTAGAACTATAAAACGTCACAATAAGATTTAGTGCTATATA
           2290                2310                2330

ATGACAAAACGCATGGTAAGAAAAGATTGGCCTTTCCCTGGAGACCCTAGTGGAAGCCGT
2341 ----------+----------+----------+----------+----------+----------+ 2400
     TACTGTTTTGCGTACCATTCTTTTCTAACCGGAAAGGGACCTCTGGGATCACCTTCGGCA
           2350                2370                2390

GTTGTCAGAAAACTTTTCGAACTTTAACAAAAGAGTATATTTAGCTTATAGTTTTTAGAA
2401 ----------+----------+----------+----------+----------+----------+ 2460
     CAACAGTCTTTTGAAAAGCTTGAAATTGTTTTCTCATATAAATCGAATATCAAAAATCTT
           2410                2430                2450

TGTTTGTTTTGTTTTTTACTAAAGTAGTACT
2461 ----------+----------+--------+--- 2492
     ACAAAACAAAACAAAAAATGATTTCATCATGA
           2470                2490
```

PHEROMONE - INDUCIBLE YEAST PROMOTER

RELATED APPLICATION

This application is a continuation-in-part application of Ser. No. 066,078, filed June 24, 1987, now abandoned.

FUNDING

Work described herein was supported by funding from the National Cancer Institute and the National Institutes of Health.

BACKGROUND

It is possible, using recombinant DNA technology, to clone and express in bacteria and yeast a variety of genes which are not present in such organisms as they occur in nature. For example, procedures for cloning DNA segments in *E. coli*, by inserting the DNA into or bacteriophage genome, are well established and frequently used to isolate prokaryotic and eukaryotic genes.

The yeast *Saccharomyces cerevisiae* (*S. cerevisiae*) is also used as a host for heterologous gene expression and protein secretion. Availability of techniques which make it possible to introduce exogenous DNA into yeast genomic DNA has made it possible to develop yeast strains which produce and secrete foreign proteins such as alpha interferon, epidermal growth factor, calf prochymosin and beta-endorphin. Heterologous eukaryotic genes can be expressed in *S. cerevisiae* if they are placed under the control of a yeast gene promoter region. Heterologous protein yields will be determined, at least in part, by the promoter chosen. As an example, the promoter from the yeast gene for phosphoglycerate kinase (PGK) has been described as directing expression of heterologous genes with efficiency at least 500-fold greater than that evident when the TRP1 promoter is used. Mellor, J. et al., *Gene*, 33:215–226 (1985). Hitzeman and co-workers describe work to increase expression of the gene encoding bovine growth hormone in yeast. The 5'-promoter region, translation signal and signal peptide sequences were replaced with yeast genomic DNA from similar regions. Hitzeman, R. A. et al., *Nature*, 295:717–722 (1981).

The type of vector chosen (e.g., a high-copy-number 2 micron plasmid-based shuttle vector, rather than an unstable high-copy-number ARS-based plasmid or a low-copy-number stable ARS/CEN plasmid) also affects yields of heterologous proteins.

The availability of yeast promoters which are efficient in directing expression of a heterologous gene and whose activity can be regulated would be desirable.

DISCLOSURE OF THE INVENTION

The present invention is based on the identification and isolation of two genes which are required for efficient cell fusion during yeast conjugation. Transcription of these two genes has been shown to be greatly induced by the presence of the appropriate mating pheromone. Expression of a gene of interest placed under the control of the promoter of either of these two genes has also been shown to be similarly induced by the presence of the appropriate mating pheromone. When the promoter-gene of interest combination is present on a high-copy vector in yeast cells stimulated by the appropriate mating pheromone, expression of the fusion product is greatly increased.

According to the present invention, DNA encoding a protein of interest is placed under the control of a yeast (e.g., *S. cerevisiae*) promoter whose transcription is induced by the appropriate mating pheromone. Induction of the yeast promoter occurs as a result of stimulation by the appropriate mating pheromone.

According to the present invention, DNA encoding the protein of interest (DNA of interest) is fused or linked to the pheromone-inducible yeast promoter, using known techniques; the promoter-DNA of interest fusion is inserted onto an appropriate vector; vectors containing the fusion are introduced into yeast cells (e.g., by transformation); and induction of transcription of the promoter is stimulated by the appropriate mating pheromone (i.e., alpha factor for a cells, a factor for alpha cells). Induction of the yeast promoter in this manner also results in expression of the DNA of interest which is under its control, resulting in production of the protein encoded by the DNA of interest. If the promoter-DNA of interest fusion is inserted onto a high copy vector (such as a high copy two micron vector), stimulation by the appropriate mating pheromone results in a significant increase in induction of the promoter-DNA of interest fusion and production of the encoded protein in substantial quantities. Thus, it is possible to clone DNA (i.e., an entire gene or a gene segment) encoding a protein or polypeptide in yeast, with expression of the DNA being controlled by the inducible promoter; the promoter's activity is, in turn, determined by the presence or absence of stimulation by the appropriate mating pheromone.

In one embodiment, a DNA fragment from either the FUS1 gene or the FUS2 gene of *S. cerevisiae*, which includes the FUS1 promoter or the FUS2 promoter, respectively, is fused or linked, using techniques known to those skilled in the art, to DNA encoding a protein of interest. The DNA fragment of the FUS1 or FUS2 gene is a 5' segment or N terminal moiety. The yeast DNA fragment-DNA of interest fusion is inserted into a vector and the vector introduced into wild-type yeast cells. Upon stimulation of the yeast cells by the appropriate pheromone, induction of transcription of the yeast gene fragment (5' segment) occurs, the DNA of interest is expressed and a fusion protein which includes the FUS1 (or FUS2)-encoded protein sequence and the protein or polypeptide encoded by the DNA of interest is produced.

For example, DNA from the FUS1 gene which includes the FUS1 promoter and sequences encoding approximately the first 254 amino acids of FUS1 is fused to DNA encoding a protein or polypeptide of interest and the resulting combination inserted onto a high copy two micron vector (to produce a FUS1-DNA of interest plasmid). The resulting plasmid is introduced into wild-type a cells, which are incubated with alpha factor. Alpha factor induces a-type cells to respond; induction of the FUS1 promoter leads to induction of transcription of the DNA of interest to which it is fused. The result is expression of the FUS1-DNA of interest fusion protein (i.e , a fusion protein which is the FUS1-encoded protein and the protein encoded by the DNA of interest) at substantial levels.

DNA encompassing the promoter from either the FUS1 gene or the FUS2 gene can be fused to DNA of interest, incorporated into an appropriate vector and introduced into yeast cells, which are incubated with the appropriate mating pheromone. Incubation in this manner causes induction of transcription of the fusion which includes the FUS1 promoter or the FUS2 promoter and DNA of interest and expression of the DNA, resulting in production of the encoded protein or polypeptide.

This approach can be used to produce proteins of interest in substantial amounts in yeast cells. The method of the present invention is particularly valuable because yeast cells containing the fusion can be grown up (cultured) passively and, after sufficient quantities of cells are produced, induced to express the fusion protein (containing the protein of interest) in substantial quantities. This is an important advantage because many foreign proteins are toxic to yeast cells.

BRIEF DESCRIPTION OF THE DRAWINGS

FIG. 4 presents the nucleotide sequence of the BIK1-FUS1 region. Position 1 corresponds to position-245 of the HIS4 gene.

FIG. 5 presents the nucleotide sequence of the FUS2 gene and the deduced amino acid sequence. It includes approximately 500 nucleotides upstream and, thus, encompasses the hexameric repeats thought to be required for regulation.

DETAILED DESCRIPTION OF THE INVENTION

Figure 1:
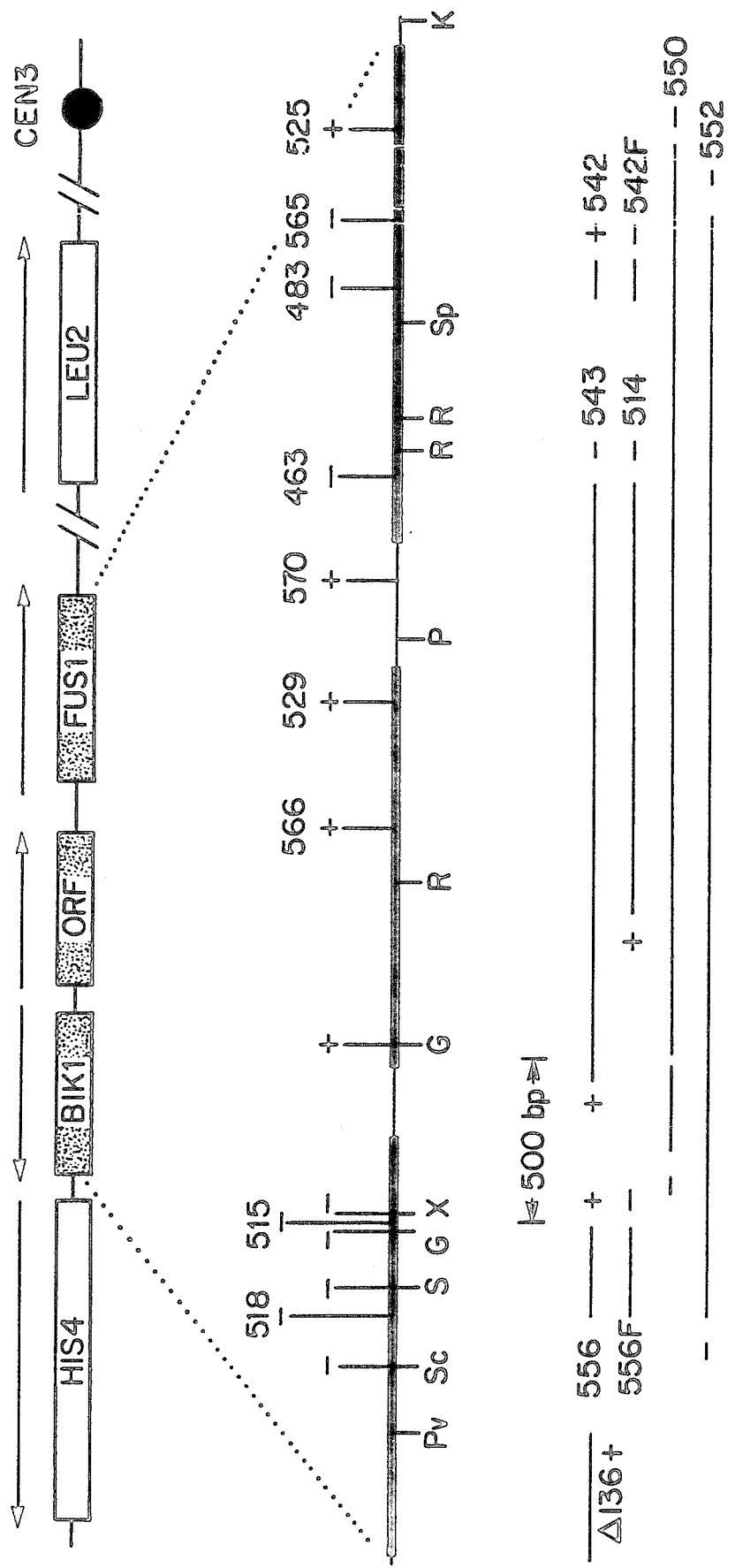
FIG. 1 is a schematic representation of chromosome III of the yeast Saccharomyces cerevisiae, on which the BIK-FUS1 region adjacent to HIS4 is shown.

The yeast S. cerevisiae can exist in a diploid or a haploid state; in the former, it has 17 pairs of chromosomes and, in the latter, a single set of chromosomes (one copy of each of the 17 chromosomes). Under favorable conditions, yeast cells exist in the diploid state and multiply rapidly. Multiplication occurs through mitosis, the process by which a diploid cell duplicates its chromosome pairs and divides into a mother cell and a bud, each of which has two copies of every chromosome.

When conditions are unfavorable, yeast cells sporulate; cells stop dividing and undergo meiosis, with the result that they duplicate their chromosome pairs and divide into four cells, each having a set of chromosomes. These haploid cells are of either the alpha type or the a type. They can reproduce by mitosis, but produce only haploids as a result. They can enter the diploid life cycle by conjugation, during which an alpha cell and an a cell fuse to form a diploid cell.

Conjugation in S. cerevisiae involves the fusion of haploid cells of opposite mating type, followed by the fusion of nuclei to form a diploid. The zygote formed by this process buds off diploid cells capable of vegetative growth. Formation of the zygote requires the coordination of two processes—cell fusion and nuclear fusion. Both processes are initiated by mating pheromones: a cells produce a-factor, to which alpha cells specifically respond, and alpha cells produce alpha-factor, to which a cells specifically respond. Duntze, W.D. et al., European Journal of Biochemistry, 35:357-365 (1973); Wilkinson, L.E. and J.R. Pringle, Experimental Cell Research, 89:175-187 (1974).

Cells stimulated by the appropriate mating pheromone produce surface agglutinins (resulting in extensive clumping of conjugating cultures), arrest their cell-cycle at the G1 stage, and elongate to form a discernible tip (a process dubbed "shmooing"). When the appropriate partners have achieved contact, presumably at the shmoo tip, the cells rapidly fuse. Cell fusion requires the degradation and/or reorganization of the cell wall and the fusion of the two plasma membranes. The nuclei subsequently fuse within the dumbbell-shaped zygote formed and the resultant diploid nucleus begins a series of division cycles, each of which yields a new diploid nucleus that enters an emerging bud. Nuclear fusion is not a passive process; like cell fusion, it requires potentiation by the mating factors. Curran, B.P.G. and B.L.A. Carter, Current Genetics, 10:943-945 (1986); Rose, M.D., et al., Molecular and Cellular Biology, 6:3490-3497 (1986).

Two genes involved in the initial zygote formation (cell surface reorganization leading to cytoplasmic fusion) have been identified. They have been designated FUS1 and FUS2. Cloning of FUS1 and FUS2 revealed that they share some functional homology. That is, FUS1 on a high copy plasmid can partially suppress a FUS2 mutant; the opposite is also true. FUS1 is essentially unexpressed in vegetative cells, but is strongly induced by incubation of haploid cells with the appropriate mating pheromone. When a cells are incubated with alpha factor, transcription of FUS1 and FUS2 is strongly induced. The same is true of FUS1 when alpha cells are induced by a factor. Mutations in these genes block the conjugation process at a point following cell contact, preventing cytoplasmic fusion and, as a result, nuclear fusion. Genes containing these mutations have been designated fus, for cell fusion defective.

The expression of these FUS genes has been shown to be activated by mating pheromones, an induction that leads to the appearance of the gene product at the tip of the shmoo. This localization suggests that the defect observed in matings between mutants is a direct result of the absence of the gene product, rather than a symptom of some general metabolic defect. Investigation of the FUS1 gene has shown that it is not expressed in vegetative haploid a and alpha cells and diploid a/alpha cells and achieves high levels only in the presence of mating pheromones, suggesting that it functions exclusively during the actual conjugation process.

Induction of the level of FUS1 mRNA was assessed to determine whether its expression is altered during conjugation. Assessment of FUS1 transcription is described in Example 1.

Similarly, when cells containing the FUS1 gene or a portion including the FUS1 promoter fused to DNA of interest are exposed to the appropriate mating pheromone (alpha factor), transcription of the FUS1 promoter is greatly induced, and leads to induction of transcription of the DNA which is under the control of the FUS1 promoter. Pheromone induction has been demonstrated by expression of a fusion protein encoded by a FUS1-LACZ fusion which has two components: a FUS1 fragment including the FUS1 promoter region and sequences encoding approximately the first 254 amino acids of FUS1 and the gene encoding beta-galactosidase. Exposure of wild-type a cells containing the fusion on a high-copy 2 micron vector resulted in at least 1000-fold induction of beta-galactosidase. When single-copy derivatives of this fusion were used, an equivalent induction ratio was observed. Pheromone induction has also been demonstrated by expression of a fusion protein encoded by a FUS1-SUC2 fusion, which includes a FUS1 fragment and the gene encoding invertase which lacks the normal signal sequence for invertase.

As a result of the work described herein, two highly inducible yeast promoters have been identified and can be used for achieving substantial levels of expression for a DNA sequence or gene of interest in yeast. The DNA sequence or gene of interest can encode a polypeptide or protein of interest (i.e., one whose expression is desired). Proteins and polypeptides of interest include those not normally expressed in yeast cells (i.e., heterologous proteins), as well as proteins normally expressed in yeast cells but at lower levels than can be achieved through use of the method of the present invention. As used herein, the term protein is meant to include proteins and polypeptides.

Recombinant DNA techniques known to those in the art are used to obtain the necessary genetic material and to introduce it into yeast cells, which are subsequently cloned. Maniatis, T., et al., *Molecular Cloning: A Laboratory Manual*, Cold Spring Harbor Laboratory, Cold Spring Harbor, NY (1982).

The DNA encoding the protein or polypeptide of interest can be isolated by obtaining mRNA of the desired gene or gene segment. For example, double-stranded DNA can be produced from the mRNA by conventional means. First, a complementary copy of the DNA is made from the mRNA, using conventional RNA technology; the RNA is subsequently removed by breaking the strands, using art-recognized methods. The cDNA is then made double-stranded; *E. coli* DNA polymerase I can be used for this step.

Synthetic linkers can be added to both ends of the double-stranded DNA (e.g., by using HindIII or EcoRI synthetic oligonucleotide linkers). cDNA having linkers at both ends is introduced into the unique site of a plasmid, which has been cut with the appropriate restriction enzyme. DNA having linkers at both ends can, alternatively, be introduced into a virus or cosmid. For example, pBR322, pM89 or lambdagtWES can be used for this purpose.

Transformation of bacteria with the ligation products will result in transformation of only a fraction of the cells. Of those cells which are transformed, only a portion will contain the recombinant plasmid. Isolation of bacteria containing the initial plasmid and the recombinant plasmid can be accomplished if the initial vector contains a selectable genetic marker, such as drug resistance (e.g., antibiotic resistance). When grown on media on which only those cells containing the selectable marker can survive (e.g., on ampicillin-containing media in the case of an ampicillin resistance marker), bacteria containing the initial plasmid and the recombinant plasmid will be the only cells to survive. A further step will be necessary to isolate cells containing the recombinant plasmid (unless the DNA of interest confers a distinguishable phenotype on cells in which it occurs). This can be done, for example, by isolating and separating DNA from transformed cells and analyzing the DNA to identify cells containing the recombinant plasmids. This can be done, for example, by electrophoresis or sequence analysis.

After the recombinant plasmid is cloned, isolated and identified, bacterial cells in which it is included can be grown, resulting in increased numbers of the recombinant plasmid.

The recombinant DNA molecule can be introduced into yeast cells, using conventional procedures. Ito, H. et al., *Journal of Bacteriology*, 153:163–168 (1983). That cells contain the recombinant DNA molecule can be verified, both by genetic and hybridization techniques.

Host cells (e.g., *S. cerevisiae*) containing the recombinant DNA molecule are then cultured (in standard media and under standard conditions); once grown, yeast cells are stimulated by the appropriate mating pheromone. This results in induction of transcription of the yeast gene fragment and expression of the protein or polypeptide of interest in substantial quantities. The protein or polypeptide is produced as part of a fusion protein, which includes the FUS1 (or FUS2)-encoded protein and the protein or polypeptide encoded by the DNA of interest. The protein or polypeptide is subsequently removed or released from the fusion protein; this can be done, for example, by including a cassette which encodes the invertase signal sequence. This results in secretion of the fusion protein, followed by removal of the signal sequence.

Vectors containing the pheromone-inducible yeast promoter and DNA of interest can be constructed. For example, a recombinant plasmid can be constructed in vitro, using known techniques. One example of such a plasmid includes: the FUS1 promoter, the initiation region of FUS1, and the gene of interest; optionally it can also contain the FUS1 signal peptide. Alternatively, a plasmid can include a 5′ segment or an N terminal moiety of the FUS1 gene which also encompasses DNA encoding approximately the first 254 amino acids; a gene of interest; a selectable marker (e.g., ura3) in yeast; a 2 micron autonomously replicating sequence (ARS); a selectable marker (e.g., amp$^r$) in bacteria and a replication origin for producing the plasmid in *E. coli*. An example of an appropriate plasmid into which the FUS1 DNA fragment can be inserted is YEp24.

In one embodiment of the method of the present invention for expressing proteins or polypeptides of interest in yeast, a DNA fragment from either the FUS1 gene or the FUS2 gene, which includes the FUS1 or the FUS2 promoter, respectively, is fused or linked to DNA or a gene encoding the polypeptide or protein (DNA of interest). The yeast DNA fragment can include nucleotide sequences in addition to those which make up the promoter sequence and, in one embodiment, also includes sequences encoding approximately the first 254 amino acids of FUS1. The resulting promoter-DNA of interest fusion is incorporated into a plasmid, using conventional methods. The DNA which includes the yeast promoter and additional sequences and the DNA encoding the protein of interest can be produced through genetic engineering techniques (e.g., by cloning), can be synthesized mechanically or can be DNA isolated from yeast cells.

The FUS1 or FUS2 promoter will generally be fused or linked to the DNA or gene (i.e., with no intervening nucleotide sequences other than those which might be needed for joining the two components). However, the promoter and the DNA or gene can be separated by intervening sequences of any length, provided the DNA or gene is under the control of the promoter.

The FUS1-gene of interest fusion or the FUS2-gene of interest fusion is inserted on an appropriate (i.e., high copy) vector, which is introduced into yeast cells by techniques known to those in the art. The vector can also include a DNA sequence encoding a characteristic, such as ability or inability to metabolize a particular nutrient or drug resistance, which makes it possible to select cells into which the vector (and, thus, the promoter-DNA of interest fusion) has been introduced and in which the DNA it contains is being expressed. Cells containing the vector are selected (e.g., by culturing on media containing a substance or lacking a nutrient whose presence or absence determines cells, ability to survive) and, after the cells have grown, exposed to the appropriate mating pheromone.

Yeast cells containing the vector are exposed to/-stimulated by the appropriate mating pheromone by the addition of essentially pure (either synthetic or naturally occurring) mating pheromone to the culture medium in which the transformed cells are grown, by the addition of a crude preparation of the appropriate mating pheromone, or by culturing with yeast cells of the opposite mating type (i.e., culturing a cells containing the vector with alpha cells producing alpha factor).

In one embodiment of a recombinant plasmid which can be used in the method of the present invention, the following components are included: a) a fragment of a plasmid, such as pBR322, which includes the plasmid DNA replication origin, which makes it possible to propagate DNA in $E.\ coli$; b) DNA encoding a selectable genetic marker (e.g., a drug resistance gene, such as $amp^r$, which makes it possible to select bacteria ($E.\ coli$) containing the recombinant plasmid; c) a fragment of the yeast 2 micron autonomously replicating sequence (ARS); d) a DNA fragment encoding a selectable genetic marker (e.g., a drug resistance gene, such as $amp^r$, ura3), which makes it possible to select yeast containing the recombinant plasmid; e) a fragment of yeast genomic DNA which includes the FUS1 promoter and sequences encoding approximately the first 254 amino acids of FUS1 and makes induction as a result of stimulation by the appropriate mating factor possible; and f) DNA encoding a protein or polypeptide not normally produced in substantial quantities in yeast cells. The latter component is positioned in the construct so as to be under the optimal control of the FUS1 promoter; induction of the FUS1 promoter leads to induction of transcription of the DNA of interest.

The promoters and the method of the present invention, can be used to express a protein of interest, such as tpa, kpa, calf renin and bovine growth hormone. The genes encoding each of these proteins can be the naturally-occurring gene or DNA encoding the protein can be synthesized. For example, as described above, the FUS1 promoter and the first 254 amino acids of FUS1 are fused, using known techniques, to the gene of interest. Maniatis, T. et al., *Molecular Cloning: A Laboratory Manual*, Cold Spring Harbor Laboratory, Cold Spring Harbor, NY (1982). They are inserted onto a 2 micron high copy plasmid and introduced into a cells, again using known methods. a cells containing the plasmid and the FUS1 promoter-gene of interest fusion are stimulated by addition of growing alpha cells. In this way, the a cells are stimulated by the alpha factor and induction of the FUS1 promoter occurs and leads to induction of the DNA encoding the protein of interest.

In a method for obtaining expression of a protein or polypeptide of interest in yeast according to the present invention, a portion of either the FUS1 or the FUS2 gene which includes the respective promoter is fused to DNA encoding the protein or polypeptide. This is done in such a way that the DNA of interest is placed under the control of the FUS! or FUS2 promoter; preferably, it is placed under the optimal control of the promoter. The fusion produced is introduced into cells, in which the genetic information is retained and passed on to subsequent generations. Construction of a yeast strain having these characteristics (a pheromone-inducible promoter linked to DNA encoding a protein or polypeptide of interest) is useful because such cells can be used (e.g., commercially) to produce the encoded products. Large-scale yeast fermentation methods are well developed and $S.\ cerevisiae$ has no disadvantageous characteristics (e.g., toxicity).

In a further embodiment of the present invention, DNA encoding protein or polypeptide of interest is introduced into yeast cells through the use of retroviral vectors containing the pheromone-inducible promoter, DNA of interest and other components necessary for expression of the encoded protein.

The host cell, in which the pheromone-inducible promoter-DNA of interest fusion is expressed, will generally be the yeast strain $S.\ cerevisiae$. $S.\ cerevisiae$ has distinct advantages, as explained previously. However, other yeast cells which can be transformed with the promoter-DNA of interest fusion can also be used.

Cultivation of yeast can be carried out under well-standardized conditions; this is the case with yeast cells into which the promoter-DNA of interest fusion is introduced. For example, yeast cells can be grown on commonly used laboratory media, such as yeast nitrogen base (YNB, Difco). Stimulation of yeast cells to induce transcription of the promoter and DNA of interest can be carried out in this media, with the addition of mating factor, or of yeast cells of the opposite mating type (which will produce the pheromone necessary to stimulate induction). In one embodiment of the present invention, approximately 8 micrograms (5 micromolar) of mating factor is included per milliliter of culture media. If yeast cells containing the FUS1 DNA fragment-DNA of interest fusion are cultured with yeast cells of the opposite mating type, an equal volume of each of the two types of yeasts is used. That is, cells of equal density and at the same stage of growth are cultured together; in this case, both types of cells are growing exponentially.

It is evident from the above description that the pheromone-inducible yeast promoter can be introduced into yeast cells, along with DNA which encodes one or more proteins of interest and transcription of which is under control of the promoter, and used to produce proteins having a wide variety of applications (e.g., as drugs, enzymes, constituents of foods and beverages).

The present invention will now be illustrated with the following examples, which are not to be seen as limiting in any way.

EXAMPLE 1

Induction of FUS1 and FUS2 by mating pheromones.

Induction of the FUS1 and the FUS2 genes was assessed as follows: For induction by alpha-factor, cells were grown to Klett 40 in YPD or SC-ura (for selection of plasmids) which had been titrated to pH 4 with hydrochloric acid. Alpha-factor (Sigma Chemical Company) was added to a concentration of 5 micromolar (uM) (1:100 dilution of a 0.5 mM solution in methanol), or methanol was added to a concentration of 1%. Cells were grown for two additional hours at 30° C., at which time more than 90% of the alpha-factor treated population had arrested as shmoos or unbudded cells.

For induction by a-factor, cells were pregrown in untitrated SC-ura to Klett 40-50, and then pelleted and resuspended in an equal volume of YPD media in which JY132 cells (MATa) or EEX8 cells (a/alpha) were growing at a similar density, or in an equal volume of unconditioned YPD. The cells were then grown for two more hours at 30° C.

Figure 2:
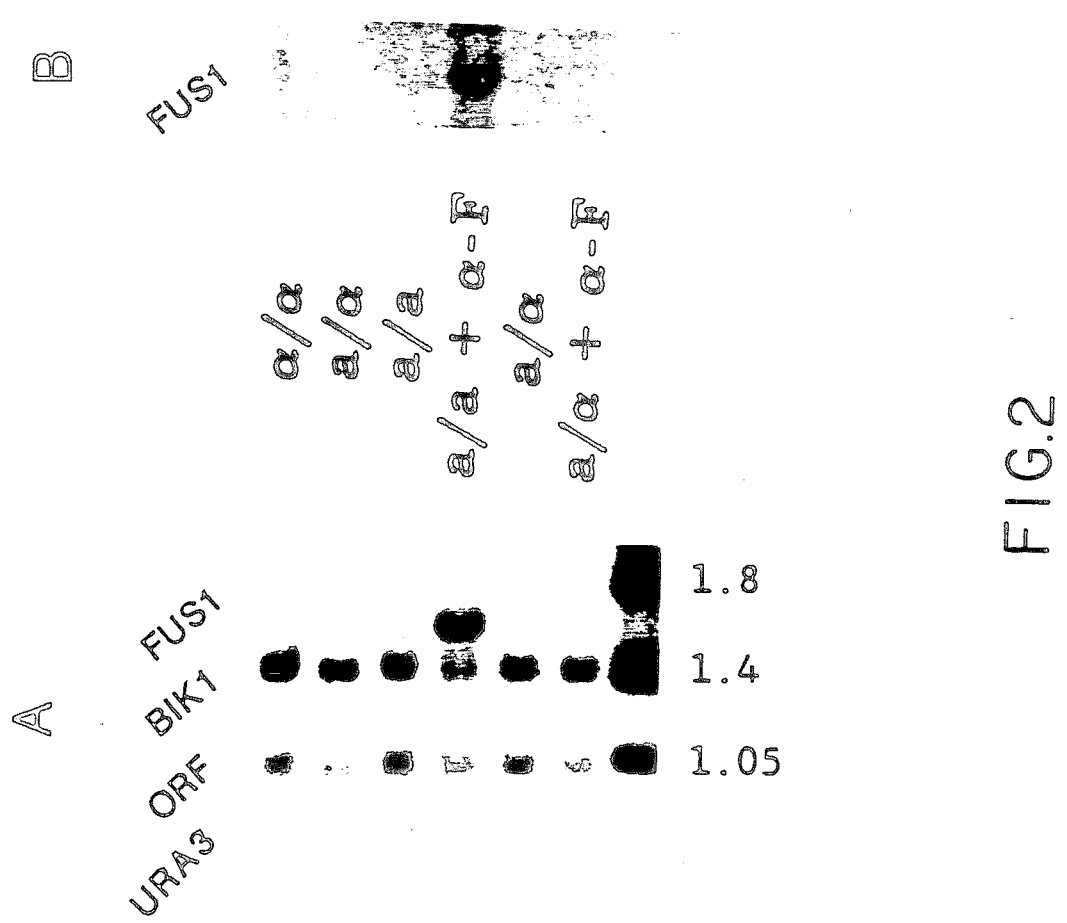
FIG. 2 shows results of Northern hybridizations of total RNA isolated from yeast strains treated with alpha-factor or solvent minus alpha-factor.

Northern analysis. Total RNA was isolated from cells treated for 2 hours with alpha-factor or from control cells using the method of Carlson and Botstein. Carlson, M. and D. Botstein, Cell, 28:145-154 (1982). The isolated total RNA was separated by electrophoresis through a 1.5% agarose denaturing gel, transferred to the nylon membrane GeneScreen Plus according to the manufacturer's instructions (New England Nuclear Research Products, Boston), and hybridized, either with labelled RNA obtained from in vitro SP6 transcription (Promega Biotec, Madison, WI) or with DNA labelled by nick translation. Maniatis, T. et al., *Molecular Cloning: A Laboratory Manual*, Cold Spring Harbor Laboratory, Cold Spring Harbor, N.Y. (1982). To obtain a single-stranded probe specific for FUS1, a fragment internal to the gene was inserted into an SP6 vector in the proper orientation and transcribed in vitro in the presence of labelled nucleotide. The RNA probe extended from nucleotide 3635 to 4030 (see FIG. 4) of the FUS1 gene. The DNA probe consisted of the BIK1-FUS1 HindIII fragment inserted into the URA3 vector YIp5. FIG. 2 shows the resultant autoradiogram, as well as a duplicate filter probed with the 6 kb HindIII fragment containing the entire FUS1-BIK1 region inserted into the URA3 vector YIp5. The addition of the alpha-factor pheromone to a/a cells, but not to isogenic a/alpha cells, caused an induction of a 1.6 kb message not observed in cells that were not exposed to the pheromone. The Northern blot on the left in FIG. 2 is a control showing that an approximately equivalent amount of RNA was loaded onto each lane. The FUS1 gene is a prototype for the FUS2 gene. The same procedure was followed using the FUS2 gene and similar results were obtained.

Beta-galactosidase assays. Cells were permeabilized by vigorous agitation in Z-buffer supplemented with 0.0075% SDS and 60 ul/ml chloroform, and the assays were performed essentially as described by Miller. Miller, J.H., *Experiments in Molecular Genetics*, Cold Spring Harbor Laboratory, Cold Spring Harbor, N.Y. (1972). Units of beta-galactosidase activity are expressed by the formula (1000×O.D.$_{420}$ of centrifuged reaction mixture)/(O.D.$_{600}$ of culture x volume of culture x minutes of assay).

EXAMPLE 2

Construction and expression of FUS1-heterologous DNA.

The pheromone effect described in Example 1 was analyzed further by the construction of a FUS1-LACZ fusion that had the promoter region of FUS1 and sequences which encode the first 254 amino acids of FUS1 fused to beta-galactosidase. Addition of alpha-factor to wild type a cells containing this fusion on a high copy micron vector led to at least a 1000-fold induction of beta-galactosidase, as shown in Table 1.

TABLE 1

| Induction of FUS1-LACZ by mating pheromone. | | |
|---|---|---|
| | Uninduced | Induced* |
| JY132(pSB234) (MATa) | 0.5 | 740 |
| JY133(pSB234) (MATalpha) | 650 | | pSB234 is a 2 micron-URA3-based plasmid which encodes the FUS1-LACZ gene product; the fusion contained the first 254 amino acids of FUS1 fused to beta-galactosidase. Units of activity were determined as described in Example 1. An equivalent induction ratio was also seen for single copy derivatives of this fusion.

Incubation of alpha cells containing the same FUS1-LACZ plasmid with wild type a cells (a source of a-factor) also caused substantial induction; the uninduced level in alpha cells appeared to be significantly higher than in a cells. The same procedure was followed using the FUS2 gene and similar results were obtained.

Figure 3:
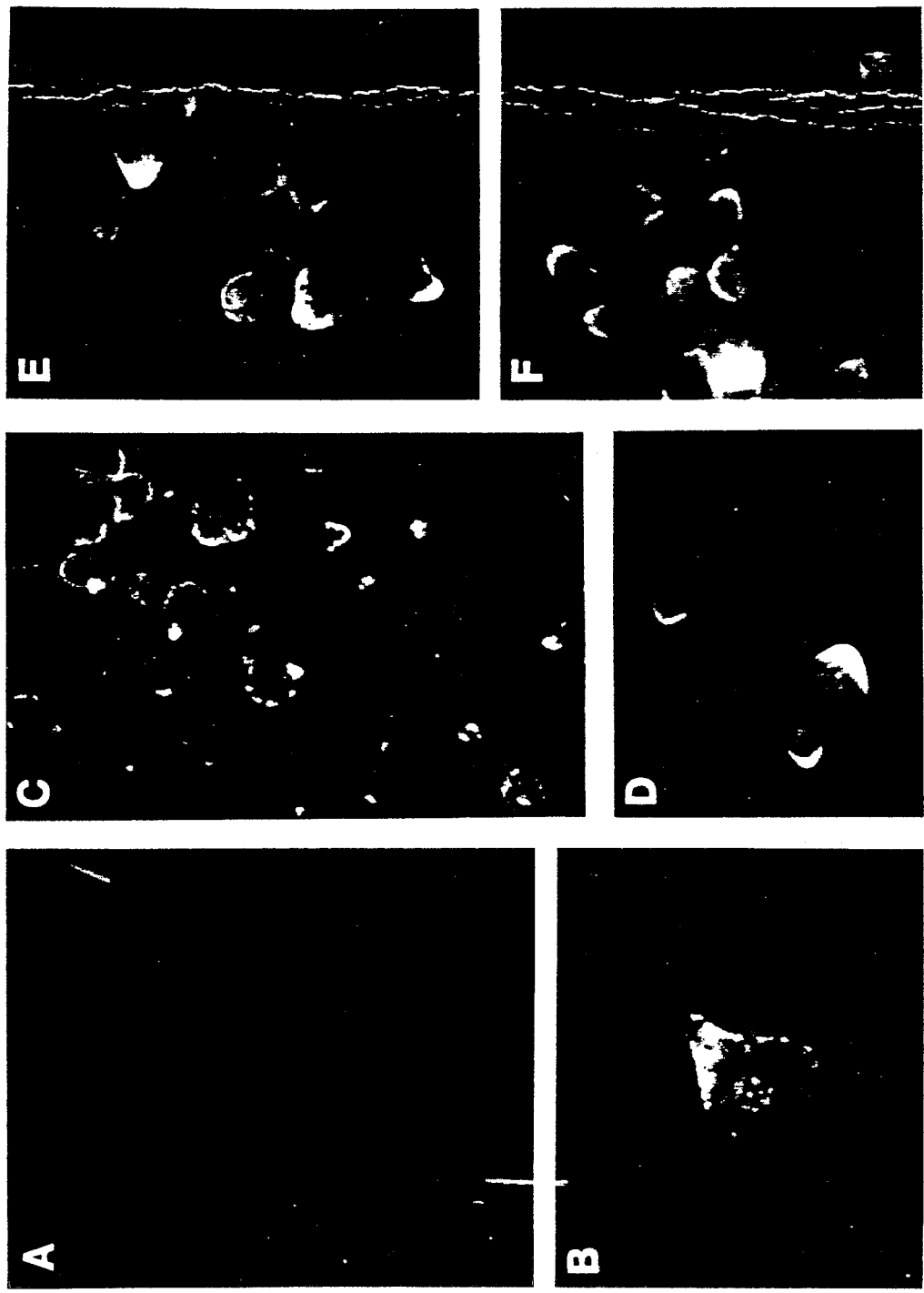
FIG. 3 are immunofluorescence micrographs of alpha-factor-induced spheroplasts fixed in formaldehyde and incubated with anti-beta-galaotosidase antibody and FITC-conjugated anti-mouse Ig.

Localization of FUS1-LACZ. The cellular location of the FUS1 gene product was determined by immunofluorescence microscopy on pheromone-treated cells containing the LacZ fusion Kilmartin, J.V. and A.E.M. Adams, *Journal of Cell Biology*, 98:922-933 (1984). A mouse monoclonal alpha-beta-galactosidase antibody (provided by T. Mason) was used as a probe. It was visualized using a FITC-conjugated goat anti-mouse antibody (Boehringer Mannheim Biochemicals, Indianapolis, IN). FIG. 3 shows a series of micrographs from such cells, with a CYC1-LACZ fusion in similarly treated cells acting as a control fusion that should be cytoplasmic. In a large fraction of the cells, the FUS1-LacZ protein appears to be located exclusively at the tip of the shmoo. The FUS2-LacZ protein was localized using similar techniques. It appears to be located within the schmoo, but not at the tip of the schmoo.

EXAMPLE 3

Determination of the sequence of the FUS1-BIK1 region.

The 6 kb HindIII fragment containing FUS1 and BIK1 was inserted into the unique HindIII site of YCp50, in the orientation bla-BIK1-FUS1-tet. Farabaugh, P.J. and G.R. Fink, *Nature*, 286:352-356 (1980). The unique BamHI site of this plasmid was subsequently destroyed by filling in the ends with Klenow fragment and religation of the blunt ends, generating pJef423. All complementation analyses were performed using derivatives of this plasmid.

Linker insertion mutagenesis was performed by DNAse I nicking, micrococcal nuclease digestion followed by digestion with S1 nuclease, and ligation of BamHI linkers, essentially as described by Shortle. Shortle, D., *Gene*. 22:181-189 (1983). The sequence of the BIK1-FUS1 region was obtained by inserting various restriction fragments, including those obtained from the BamHI insertions, into the M13 phage derivatives mp18 and mp19, and sequencing by the dideoxy chain termination method. Biggin, M.D. et al., *Proceedings of the National Academy of Sciences, U.S.A.*, 80:3963-3965 (1983); Sanger, F. et al., *Proceedings of the National Academy of Sciences, U.S.A.*, 74:5463-5467 (1977).

The precise structure of the cloned FUS1 gene was determined by dideoxy sequencing of a collection of M13 mp18 and M13 mp19 phage containing different segments of the entire region, including BIK1 sequences. The sequence is presented in FIG. 4. Except for small stretches of the intervening open reading frame, sequencing was carried out on both strands of the DNA. The sequence differs at four positions between nucleotides 519 and 540 from that previously determined. Donahue, T.F. et al., *Gene*, 18:47-59 (1982). In three of these positions, an extra T was determined to occur and at one position, a T rather than an A was found. The sequence of this region is: GTAGCTGTT-CATTCTCAGCGTC. The BIK1 coding region extends to within 14 bases of the first upstream repeat (TGACTC) of the HIS4 gene.

The FUS1 and FUS2 genes were isolated as described below. For FUS1, this was done as follows: A yeast strain (L1052) containing a large deletion (Δ453) extending from HIS4 to LEU2 was transformed with various derivatives of pJef423 harboring linker insertions. These transformants were assayed by the replica-plating test for their ability to mate successfully with a Δ453 tester lawn, L1546. Large linker-associated deletions (e.g. 550, 552; FIG. 1) in the HindIII fragment completely abolished the ability of the plasmid to complement the Δ453 defect; however, less extensive linker-associated deletions (e.g. 514, 543) and "simple" linker insertions (less than 50 bp deleted; 518, 483) only partially compromised the complementing activity of the HindIII insert. From this mutational analysis, a portion of which is presented in FIG. 1, a map was constructed which contains two distinct regions of complementing activity; either region alone is able to restore only partial mating competence to the Δ453 recipient.

With the exception of 565, 566, 514, and Δ136, all of the mutations shown in FIG. 1 were integrated into the chromosome of wild type cells (JY132 and JY133). The linker insertions were moved to URA3 integrating vectors, and the resultant plasmids were directed to integrate at chromosome III by cutting at the unique KnpI site before transformation. Orr-Weaver, T.L. et al., *Proceedings of the National Academy of Sciences, U.S.A.*, 78:6354-6358 (1981).

The recipient strains harbored the his4-34 mutation, which lies within the region of his4 that is duplicated upon integration of these plasmids. Therefore, His+ recombinants were selected for, in order to obtain the appropriate "loop-out" excision event. Those His+ derivatives which had simultaneously become Ura− harbored the appropriate linker insertion (or frame-shifted restriction site) and no plasmid sequences. Complementation tests using these strains transformed with the original set of pJef423 derivatives confirmed the idea that two genes required for efficient mating (FUS1 and FUS2) reside on the HindIII fragment upstream from HIS4.

The fus2-1 mutation was uncovered in a cross between C52a and JY145 (fus1-483). Several tetrads from this cross produced one ascospore which, when mated to Δ453 lawns, displayed a drastic defect as compared to the response with wild type lawns. (fus1 alone displays only a partial defect when mated to Δ453). These segregants were outcrossed to wild type strains, and the segregation of wild type (good mating with all lawns), partially defective (poor mating with mutant parent lawns, but partial mating with fus1 lawns), and completely defective (poor mating with fus1 lawns and with mutant parent lawns) phenotypes among the spore clones suggested the presence of two unlinked fus mutations in the mutant parent. Single fus mutants mate poorly with double mutants, but partially with single mutants, and conversely, double mutants mate poorly with single mutants and double mutants (but mate well with wild type). The mating type of mutants does not affect their phenotype as assayed by replica plating.

The fus1 mutation was identified in strains carrying a deletion extending from HIS4 to LEU2 (FIG. 1). This large deletion, designated Δ453, had no obvious effect on the vegetative growth of the cells, but subsequent genetic manipulations revealed that Δ453 strains form diploids at greatly reduced rates with strains carrying the same deletion, but at relatively normal rates with wild type strains. A centromere plasmid bearing the 6 kb HindIII fragment beginning in HIS4 and extending towards LEU2, subcloned from a 15 kb HIS4 BamHI-EcoRI fragment (isolated by "eviction"), was found to restore normal mating to a Δ453 strain (L1052), suggesting that this segment contains the mating functions missing from Δ453. Donahue, T.F. et al., *Cell*, 32:89-98 (1983).

Extensive deletion analysis and random linker insertion mutagenesis (a subset of which is presented in FIG. 1) reveal that the phenotype of Δ453 results from deletion of two separate genes, both of which are located on the HindIII fragment. The genes were further defined by introducing the linker insertions into the chromosome of wild type cells and analyzing the behavior of the resulting strains in crosses. The linker insertions fall into two groups based on complementation tests. Insertions in one of these groups leads to a block in cellular fusion in crosses between members of the same group. The gene defined by this complementation group is called fus1. Mutants in the second group mate normally with wild type and fus1 mutants; however, in crosses with members of the same complementation group, the cells fuse normally but their nuclei fail to fuse. The gene defined by this complementation group is called bik1 (bilateral karyogamy defect). These experiments showed that the mating defect of Δ453 results from the deletion of two genes: BIK1 and FUS1, each of which has its own unique function (see FIG. 1).

Isolation of FUS2 was carried out as follows: The fus2 mutation was uncovered in crosses of fus1 by strain C52a, obtained from C. Nombela. The phenotype of fus1 mutants is rather leaky; many pairs in a fus1×fus1 cross fuse their nuclei despite the abnormal bridge between the pair. In crosses of JY146 (alpha fus1-483 ura3-52 leu2-3, 112) by C52a (a exb1-1) several ascospore segregants were obtained which displayed a much more severe fusion defect than that of the fus1 mutant. These segregants were shown by genetic analysis to be double mutants, fus1 fus2. The fus2 mutation was apparently present in C52a, although it is not linked to the exb1-1 mutation described by Santos et al. (as assayed by the methylumbelliferyl-beta-D-glucoside overlay technique). As shown by subsequent tests, fus2 has a phenotype similar to that of fus1.

To clone the FUS2 gene, the severe mating defect of a fus2 mutant when mated with a fus1 fus2 double mutant was used. A FUS+ strain can readily mate with a fus double mutant in the replica plating assay and the fus2 defect is recessive; as a result, cloning by complementation is straightforward. A MATa fus2 strain (JY306) was used as a recipient in transformation with the Yep24 library of Carlson and Botstein. Carlson, M. and D. Botstein, *Cell*, 28:145-154 (1982). A clone (pSB257) was identified (out of about 2000 screened) which restored normal mating function to fus2 when mated to fus1 fus2 (JY217). Genetic analysis demonstrates that the 9 kb DNA segment isolated corresponds to FUS2: crosses between FUS+ strains and a fus2 strain harboring a FUS2+-URA3+ plasmid integrated at fus2 yielded 19 out of 21 tetrads which contain 4 FUS spores. One-step gene disruption by the substitution of an internal 1.1 kb HindIII fragment with the URA3 gene resulted in a phenotype identical to that of fus2-1: a gross mating defect with fus1 fus2 strains, but only slightly reduced diploid formation with either fus2-1 or fus2::URA3 strains.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A DNA fragment comprising the promoter of the FUS1 gene isolated from *Saccharomyces cerevisiae*, operably linked to DNA encoding at least one polypeptide not normally expressed at substantial levels in Saccharomyces cells, transcription of the Saccharomyces promoter inducible by a Saccharomyces mating pheromone, for directing the expression of the polypeptide-encoding DNA in Saccharomyces cells.

2. A DNA fragment comprising the promoter of the FUS2 gene isolated from *Saccharomyces cerevisiae*, operably linked to DNA encoding at least one polypeptide not normally expressed at substantial levels in Saccharomyces cells, transcription of the Saccharomyces promoter inducible by a Saccharomyces mating pheromone, for directing the expression of the polypeptide-encoding DNA in Saccharomyces cells.

3. A DNA fragment of claim 1 additionally comprising a nucleotide sequence encoding the first 254 amino acids of the FUS1 gene.

4. A DNA fragment of claim 3 additionally comprising a nucleotide sequence encoding the first 617 amino acids of the FUS2 gene.

5. A DNA fragment comprising a Saccharomyces promoter of a gene required for cell fusion during Saccharomyces conjugation, wherein the Saccharomyces promoter has the sequence consisting essentially of nucleotides 2550 to 3224 of FIG. 4 and is operably linked to DNA encoding at least one polypeptide not normally expressed at substantial levels in Saccharomyces cells, transcription of the Saccharomyces promoter inducible by a Saccharomyces mating pheromone, for directing the expression of the polypeptide-encoding DNA in Saccharomyces cells.

6. A DNA fragment comprising a Saccharomyces promoter of a gene required for cell fusion during Saccharomyces conjugation, wherein the Saccharomyces promoter has the sequence consisting essentially of nucleotides 1 to 402 of FIG. 5 and is operably linked to DNA encoding at least one polypeptide not normally expressed at substantial levels in Saccharomyces cells, transcription of the Saccharomyces promoter inducible by a Saccharomyces mating pheromone, for directing the expression of the polypeptide-encoding DNA in Saccharomyces cells.

7. A DNA fragment comprising a Saccharomyces promoter of a gene required for cell fusion during Saccharomyces conjugation, wherein the Saccharomyces promoter has the sequence consisting essentially of nucleotides 2550 to 3987 of FIG. 4 and is operably linked to DNA encoding at least one polypeptide not normally expressed at substantial levels in Saccharomyces cells, transcription of the Saccharomyces promoter inducible by a Saccharomyces mating pheromone, for directing the expression of the polypeptide-encoding DNA in Saccharomyces cells.

8. A DNA fragment comprising a Saccharomyces promoter of a gene required for cell fusion during Saccharomyces conjugation, wherein the Saccharomyces promoter has the sequence consisting essentially of nucleotides 1 to 2253 of FIG. 5 and is operably linked to DNA encoding at least one polypeptide not normally expressed at substantial levels in Saccharomyces cells, transcription of the Saccharomyces promoter inducible by a Saccharomyces mating pheromone, for directing the expression of the polypeptide-encoding DNA in Saccharomyces cells.

9. Isolated DNA having the sequence consisting essentially of nucleotides 2550 to 3224 of FIG. 4.

10. Isolated DNA having the sequence consisting essentially of nucleotides 2550 to 3987 of FIG. 4.

11. Isolated DNA having the sequence consisting essentially of nucleotides 1 to 402 of FIG. 5.

12. Isolated DNA having the sequence consisting essentially of nucleotides 1 to 2253 of FIG. 5.

13. The promoter of the FUS1 gene isolated from *Saccharomyces cerevisiae* operably linked to DNA encoding a protein or a polypeptide not normally expressed at substantial levels in Saccharomyces cells.

14. The promoter of the FUS2 gene isolated from *Saccharomyces cerevisive*, operably linked to DNA encoding a protein or polypeptide not normally expressed at substantial levels in Saccharomyces cells.

15. A recombinant DNA sequence which is nucleotides 2550 to 3987 of FIG. 4 fused with X, wherein X is DNA encoding a protein or a polypeptide not normally expressed at substantial levels in yeast cells.

16. A recombinant DNA sequence which is nucleotides 1 to 2253 of FIG. 5 fused with X, wherein X is DNA encoding a protein or a polypeptide not normally expressed at substantial levels in yeast cells.

17. A recombinant DNA sequence which is nucleotides 2550 to 3224 of FIG. 4 fused with X, wherein X is DNA encoding a protein or a polypeptide not normally expressed at substantial levels in yeast cells.

18. A recombinant DNA sequence which is nucleotides 1 to 402 of FIG. 5 fused with X, wherein X is DNA encoding a protein or a polypeptide not normally expressed at substantial levels in yeast cells.

19. The recombinant DNA sequence of claim 15, wherein the polypeptide is beta-galactosidase.

20. The recombinant DNA sequence of claim 16, wherein the polypeptide is beta-galactosidase.

21. The recombinant DNA sequence of claim 17, wherein the polypeptide is beta-galactosidase.

22. The recombinant DNA sequence of claim 18, wherein the polypeptide is beta-galactosidase.

23. A method of expressing a protein or a polypeptide in Saccharomyces cells, comprising the steps of:
   a) introducing into Saccharomyces cells a recombinant vector which contains a DNA fusion, the DNA fusion comprising the pheromone-inducible Saccharomyces promoter of the FUS1 gene isolated from *Saccharomyces cerevisive*, said promoter operably linked to DNA encoding a protein or a polypeptide to be expressed in the Saccharomyces cells; and
   b) stimulating Saccharomyces cells containing the recombinant vector with the appropriate mating pheromone.

24. A method of claim 23 wherein the recombinant vector is a recombinant two micron Saccharomyces vector.

25. A method of claim 24 wherein the yeast cells are wild type a Saccharomyces cells and the mating pheromone is alpha factor.

26. A method of claim 24 wherein the yeast cells are wild type alpha Saccharomyces cells and the mating pheromone is a factor.

27. A recombinant Saccharomyces cell containing an expression vector, the expression vector comprising a DNA fragment including the pheromone-inducible promoter of the FUS1 gene isolated from *Saccharomyces cerevisive*, said promoter operably linked to DNA encoding a protein or polypeptide of interest, said protein or polypeptide not normally produced in significant amounts in Saccharomyces cells.

28. A recombinant plasmid comprising:
   a. the FUS1 promoter isolated from *Saccharomyces cerevisiae*;
   b. DNA encoding approximately the first 254 amino acids of said FUS1 gene;
   c. DNA encoding a protein or a polypeptide of interest, the DNA positioned so as to be under the control of said FUS1 promoter;
   d. DNA encoding a selectable marker in yeast;
   e. a two micron autonomously replicating sequence;
   f. DNA encoding a selectable marker in bacteria; and
   g. a replication origin for producing the plasmid in bacteria.

29. A recombinant plasmid comprising:
   a. the FUS2 promoter isolated from *Saccharomyces cerevisiae*;
   b. DNA encoding approximately the first 614 amino acids of said FUS2 gene;
   c. DNA encoding a protein or a polypeptide of interest, the DNA positioned so as to be under the control of said FUS2 promoter;
   d. DNA encoding a selectable marker in yeast;
   e. a two micron autonomously replicating sequence;
   f. DNA encoding a selectable marker in bacteria; and
   g. a replication origin for producing the plasmid in bacteria.

30. Plasmid YEp24 having inserted therein the recombinant DNA sequence of claim 15.

31. Plasmid YEp24 having inserted therein the recombinant DNA sequence of claim 16.

32. Plasmid YEp24 having inserted therein the recombinant DNA sequence of claim 17.

33. Plasmid YEp24 having inserted therein the recombinant DNA sequence of claim 18.

* * * * *

UNITED STATES PATENT AND TRADEMARK OFFICE
CERTIFICATE OF CORRECTION

PATENT NO. : 5,063,154
DATED : November 5, 1991
INVENTOR(S) : Gerald R. Fink, Joshua Trueheart and Elaine A. Elion It is certified that error appears in the above-identified patent and that said Letters Patent is hereby corrected as shown below:

Column 13, line 1,"Claim 4 depends on Claims 2, not Claim 3".

Signed and Sealed this

Thirtieth Day of March, 1993

*Attest:*

STEPHEN G. KUNIN

*Attesting Officer*  *Acting Commissioner of Patents and Trademarks*